United States Patent [19]

Bachynsky et al.

[11] Patent Number: 5,036,102

[45] Date of Patent: Jul. 30, 1991

[54] METHOD OF TREATING AUTOIMMUNE DISEASES COMPRISING ADMINISTRATION OF PSORALEN DOSAGE FORMS

[75] Inventors: Maria O. Bachynsky, Nutley; Martin H. Infeld, Upper Montclair; Richard J. Margolis; Dennis A. Perla, both of Wayne, all of N.J.

[73] Assignee: Hoffmann-La Roche Inc., Nutley, N.J.

[21] Appl. No.: 582,467

[22] Filed: Sep. 14, 1990

Related U.S. Application Data

[62] Division of Ser. No. 336,179, Apr. 11, 1989, Pat. No. 4,999,375.

[51] Int. Cl.$^5$ .............................................. A61K 31/35
[52] U.S. Cl. .................................. 514/455; 514/863; 514/825; 514/864; 514/903
[58] Field of Search ............... 514/455, 863, 860, 864, 514/825, 903

[56] References Cited

U.S. PATENT DOCUMENTS

| | | | |
|---|---|---|---|
| 4,147,703 | 4/1979 | Liebman et al. | 549/282 |
| 4,321,919 | 3/1982 | Edelson | 604/6 |
| 4,454,152 | 6/1984 | Barry et al. | 514/455 |
| 4,612,007 | 9/1986 | Edelson | 604/5 |
| 4,613,322 | 9/1986 | Edelson | 604/6 |
| 4,683,889 | 8/1987 | Edelson | 128/395 |
| 4,684,521 | 8/1987 | Edelson | 424/529 |
| 4,727,027 | 2/1988 | Wiesehahn et al. | 435/173 |
| 4,826,967 | 5/1989 | Glass | 536/23 |
| 4,913,901 | 4/1990 | Schlager | 424/78 |

FOREIGN PATENT DOCUMENTS

2052980 of 0000 United Kingdom .

OTHER PUBLICATIONS

Chemical Abstracts 97:11747c.
Edelson, Scientific American, Aug. 1988, pp. 68.
Dover et al., Archives of Dermatology, vol. 122:763 (1986).
Sullivan et al., Archives of Dermatology, vol. 112:768 (1986).
Monbaliu, et al., Dermatologica 163:468 (1981).
Edelson, et al., New England Journal of Medicine, 316:297 (1987).

*Primary Examiner*—Richard L. Raymond
*Assistant Examiner*—Gary E. Hollinden
*Attorney, Agent, or Firm*—George M. Gould; William H. Epstein; Patricia S. Rocha

[57] ABSTRACT

A method of treating leukocyte mediated autoimmune and skin diseases using psoralen reagent composition comprising sterile aqueous solutions suitable for extracorporeal administration to blood from a subject being treated by ultraviolet-A photophoresis.

4 Claims, No Drawings

METHOD OF TREATING AUTOIMMUNE DISEASES COMPRISING ADMINISTRATION OF PSORALEN DOSAGE FORMS

This is a division of application Ser. No. 07/336,179, filed Apr. 11, 1989 now U.S. Pat. No. 4,999,375 issued Mar. 12, 1991.

TECHNICAL FIELD

This invention is directed to reagent compositions of psoralen comprising sterile aqueous solutions suitable for extracorporeal administration to blood from a subject being treated by ultravoilet-A photophoresis.

The instant invention is also directed to methods for alleviating a leukocyte mediated condition by treating a subject undergoing ultraviolet-A photophoresis with the extracorporeally administered psoralen reagent composition of the invention.

BACKGROUND OF THE INVENTION

Psoralen is a linear three ring heterocyclic compound of the general structure

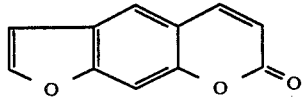

It is a bifunctional photoreactive molecule which forms covalent bonds with nucleic acids in the presence of near ultraviolet light. Psoralen's ability to react with DNA has given it clinical importance in the treatment of various skin disorders, and its ability to form interstrand crosslinks in double stranded DNA has made it a useful agent in the study of nucleic acid structure and function.

For over 10 years, patients with psoriasis have been treated with orally administered psoralens and subsequently irradiated with long wave ultraviolet-A radiation (PUVA). Currently, the only psoralen commercially available for oral administration is 8-methoxypsoralen (8-MOP). Since psoralens are lipophilic compounds, poorly soluble in water, one current oral preparation consists of 8-MOP mixed with polyethylene glycols in a soft gelatin capsule. The oral absorption of 8-MOP from this dosage form varies considerably between individuals, so peak serum psoralen levels may occur as early as 1 hour or as late as 4 hours after the capsule is administered. The subject is treated with ultraviolet A irradiation approximately two hours after oral administration of the dosage form. Because the oral absorption of 8-MOP from the capsule is variable, serum levels of 8-MOP at 2 hours post dosing may not be optimal. Since serum levels of 8-MOP and photosensitivity are directly correlated, less than optimal 8-MOP serum levels may be one factor in a poor response to PUVA therapy.

Other routes of administration for 8-MOP have been used. In the United States 8-MOP is available as a topical lotion. In Europe 8-MOP has been applied topically using baths. PUVA baths are effective but inconvenient, and topical absorption of 8-MOP is variable resulting in a lack of predictability of the phototoxic response. PUVA baths have thus not gained wide appeal.

Serum levels and photosensitivity are more predictable with rectally administered 8-MOP resulting in good therapeutic response. However, the inconvenience of rectal administration is likely to deter widespread popularity.

Other oral dosage forms comprise solutions of psoralens dissolved in alcohols and/or polyethylene glycols or are oil-on-water emulsions; or are semi-solid capsule dosage forms wherein the average crystal size of the psoralen is greatly reduced. These dosage forms have improved the consistency of PUVA therapy but the unpredictability of oral administration of psoralens still results in inconsistent responses to photophoresis therapy.

Accordingly, there is still a need for a psoralen dosage form which provides consistent results when psoralens are used in conjunction with ultraviolet-A phototherapy to alleviate disease.

SUMMARY OF THE INVENTION

The instant invention is directed to a psoralen reagent composition comprising a sterile aqueous solution of an effective minor amount of a psoralen sufficient to provide therapeutic blood levels in a subject, ethyl alcohol, propylene glycol and optionally a buffer system, said composition being suitable for extracorporeal administration to blood from a subject being treated by ultraviolet-A photophoresis.

The instant invention is also directed to a psoralen reagent composition comprising a sterile aqueous solution of an effective minor amount of a psoralen sufficient to provide therapeutic blood levels in a subject, ethyl alcohol, propylene glycol and optionally a buffer system, said composition being stored in a container suitable for extracorporeally administering a unit dose of the composition to blood from a subject being treated by ultraviolet-A photophoresis.

The instant invention is also directed to methods for alleviating leukocyte mediated diseases by treating a subject undergoing ultraviolet-A photophoresis with the extracorporeally administered psoralen reagent composition

Definitions

1. Photophoresis means extracorporeal phototherapy wherein blood is withdrawn from a subject and separated into leukocyte and leukocyte poor fractions. The erythrocytes (leukocyte poor fraction) are immediately returned to the patient and the leukocyte rich fraction is subjected to ultraviolet energy and returned to the patient.

2. Ultraviolet A means light energy from the ultraviolet A spectrum ranging from 3,200–4,000 Angstroms (A).

3. Leukocyte rich means the leukocyte rich fraction of blood from which the erythrocytes and non-leukocyte constituents have been removed.

4. Leukocyte mediated conditions means diseases or medical conditions wherein manipulation of leukocyte function with psoralen and Phototherapy results in alleviation of the disease or condition, including, for example, Cutaneous T-Cell Lymphoma (CTCL), Chronic Lymphocytic Leukemia (CLL), Scleroderma, Systemic Lupus Erythematosis (SLE), Psoriasis, Pemphigus, Psoriatic Arthritis, Atopic Dermatitis, Adult T-Cell Leukemia (ATL), AIDS (ARC), Rheumatoid Arthritis, Multiple Sclerosis (MS), cardiac transplant rejection, organ transplant rejections such as kidney, liver, etc.

5. Subject means human being.

DETAILED DESCRIPTION

The reagent composition of the invention contains the desired psoralen dissolved in alcohol, propylene glycol and water. Psoralen solutions prepared in the pH range 2 to 6 are preferred since it appears that psoralens, particularly 8-MOP, tend to be more unstable in basic solution. However, psoralen solutions at pH values outside this pH range may also acceptable. Solutions may be buffered with buffers such as acetate, lactate, phosphate, benzoate, malate, citrate, or any other suitable buffer that will maintain the pH in the desired range, although acetate is preferred. The final psoralen solution is adjusted to pH with suitable acids and/or bases. The solution is filtered to achieve sterility. Because the psoralen formulations of the invention contain a very low concentration of psoralen, it is critical that the rubber stopper used to stopper the vial stored formulations be treated in order to prevent the psoralen from being adsorbed onto or absorbed into the stopper as well as to prevent leaching of the stopper components into the solution. Rubber stoppers treated with an impervious film are suggested. Butyl stoppers with a fluoro-resin (teflon) film are preferred.

The sterile psoralen reagent composition of the invention may also be in a lyophilized form. Lyophilization is an excellent way to obtain a sterile dosage form which can be maintained stable for long periods of time. Upon reconstitution in an appropriate solvent, the psoralen solution is then suitable for use. In lyophilized formulations according to the invention, bulking agents known for this purpose such as mannitol, sodium chloride, or dextrose are dissolved in the psoralen solution in water. Acceptable acids and bases are used to adjust the pH to the preferred range, after which water to volume is added. This solution is filtered and placed into vials, lyophilized in the usual manner, stoppered and sealed.

A minor amount of the concentration of the psoralen in the formulated solution may vary as desired. However, when psoralens are administered extracorporeally only very small amounts are needed to achieve the preferred blood levels ranging from 25-500 nanograms/ml, most preferably 50-100 nanograms/ml. Thus a minor amount of psoralens constitutes a solution containing 10 μg/ml to 1 mg/ml of psoralen, most preferably 20 μg/ml solutions are recommended.

The instant invention is also directed to psoralen reagent compositions comprising sterile aqueous solutions stored in a container suitable for administering a unit dose of the composition to a subject being treated by ultraviolet-A photophoresis. Containers suitable for administering unit doses of psoralens may be syringes, ampuls, or vials, and more specifically, light resistant glass vials, for example amber vials, stored with the teflonized stoppers are preferred. The appropriate amount of the reagent composition is added to the ampul or vial which is then stoppered with teflonized stopper, sealed and sterilized. To achieve the blood levels of psoralen desired in phototherapy, a suitable vial containing about 10 ml of an approximately 20 μg/ml solution of psoralen, specifically 8-MOP, is preferred.

8-MOP is the preferred psoralen for the reagent composition although other psoralen derivatives are acceptable. 8-MOP may be obtained from natural sources, namely from the fruit of the Ammi Majus Linn plant. See, for example, Fahmy et al., "Ammi Majus Linn. Pharmacognostical Study and Isolation of Crystalline Constituent, Ammoidia", Quant. J. Pharm. and Pharmacol., 20:281, (1948). In addition, synthetic processes for psoralens are described in U.S. Pat. No. 4,130,568.

Phototherapy according to the instant invention consists of withdrawing blood from the subject who is being treated and extracorporeally administering an effective amount of the reagent composition of the invention. Generally, one or more vials containing 10 ml of a 20 μg/ml solution or 50 ml of a 20 μg/ml solution will provide the necessary blood concentration for effective phototherapy. The composition may be added to the subject's blood just after withdrawal from the body and prior to separation of the blood into leukocyte rich and leukocyte poor fractions; or the composition may be added to only the leukocyte rich fraction just prior to irradiation. Preferably, the psoralen is added just after the blood is withdrawn from the subject to allow more time for the psoralen to become distributed throughout the blood which is removed for photophoresis.

The leukocyte rich fraction of the patient's blood containing the psoralen is then irradiated with ultraviolet radiation in the wavelength range from about 2,000-4,000 A and preferably from 3,200-4,000 A. An effective amount of psoralen consists of that amount which will be capable of binding to the lymphocyte nucleic acids and, after irradiation, intercalating into the cellular DNA. Prior to ultraviolet irradiation, or activation, psoralens generally have little or no effect on cell chemistry. After irradiation the extracorporeally administered psoralen will complex with and inactivate the cellular nucleic acids resulting in inhibition of the metabolic functions of the cell. Death of the cell results due to its inability to divide. Cells undergoing the most intense metabolic activity are most prone to disablement by the psoralen photophoresis process.

The methods set forth in U.S. Pat. Nos. 4,321,919; 4,612,007; 4,683,889; 4,613,322; and 4,684,521; all incorporated by reference, illustrate phototherapy processes wherein the reagent composition of the invention may be utilized.

The instant invention is also directed to methods for alleviating leukocyte mediated diseases by treating a subject undergoing ultraviolet-A photophoresis with the extracorporeally administered psoralen reagent composition of the invention.

Phototherapy in conjunction with psoralens is known to be effective in alleviating a wide variety of leukocyte mediated conditions. (See *New England Journal of Medicine.* 316:297 (1987); and *Scientific American.* August 1988, p. 68). For example, CTCL, a lymphocyte mediated condition that manifests itself in skin lesions, can be effectively treated with 8-MOP/ultraviolet-A photophoresis therapy. The psoralen reagent composition of the invention (preferably 8-MOP) may be administered to the subject's blood just after it is withdrawn and prior to the separation of the blood into leukocyte rich and leukocyte poor fractions. This allows more time for the 8-MOP to become distributed throughout the blood constituents. The blood is then separated into the leukocyte rich and leukocyte poor fractions and the leukocyte rich fraction is then photoactivated by ultraviolet-A energy. This photoactivation causes nucleated cells which have absorbed 8-MOP to form cross-links between nitrogen bases on adjacent strands of the DNA helix. This cross-linking prevents the replication of the abnormal lymphocyte population. Non-nucleated blood components such as red blood cells contain no DNA and are thus not affected. The exposed blood fraction containing the lymphocytes neutralized by photoactivated cross-linking is returned to the patient. Animal studies suggest that the return of these cross-linked cells stimulates an immune response and substantially reduces the growth of specific lymphocyte subpopulations. The frequency of each treatment may vary widely depending upon the needs of the patient. In some instances, therapy three times a week may be necessary while in other instances, two therapies every five weeks may be sufficient. In the typical schedule, patients received photophoresis treatment every fifth week on two consecutive days.

Other leukocyte mediated conditions which respond to photophoresis therapy according to the invention are: CLL, Scleroderma, SLE, Psoriasis, Pemphigus, Psoriatic Arthritis, Atopic dermatitis, ATL, AIDS (ARC), Rheumatoid Arthritis, MS, or cardiac transplant rejection and organ transplant rejections such as kidney, liver, etc. In these instances, the reagent composition of the invention is extracorporeally administered to the patient's blood. It is generally necessary to have a blood psoralen concentration of 50–100 nanograms per ml to establish effective treatment. Wider ranges such as 25–500 nanograms per ml are acceptable, however.

The present invention will be further described in connection with the following examples which are set forth for purposes of illustration only.

EXAMPLE 1

| Preparation of 20 µg/ml 8-MOP Solution | |
|---|---|
| Ingredients | per ml |
| 8-MOP | 0.02 mg |
| Alcohol, USP (200 proof) | 0.05 ml |
| Propylene Glycol | 50.00 mg |
| Water for Injection Q.S. | 1.00 ml |

Add and dissolve 8-MOP in alcohol, USP, with mixing. Add and incorporate propylene glycol with mixing. Add sufficient water for injection to bring to the specified volume and then mix to ensure homogeneity. Filter through a suitable bacteria retentive filter into a sterile receiver. Aseptically fill into sterile vials, stopper, seal, and terminally sterilize.

EXAMPLE 2

Preparation of acetate buffered 20 µq/ml 8-MOP solutions

These solutions were prepared with buffers in the pH range 3.5–5.5, since research in our laboratories has shown that 8-MOP may be more stable when kept in acidic solution. More specifically, solutions were prepared at pH 3.5, 4.5, 5.0 and 5.5.

A. Formulation

| Ingredients | per mL |
|---|---|
| 8-MOP | 0.02 mg |
| Alcohol, USP (200 proof) | 0.05 ml |
| Propylene Glycol | 50.00 mg |
| Acetic Acid | 0.0012 ml |
| Sodium Hydroxide Solution, 10% w/v* | q.s. pH |
| Sodium Acetate** | q.s. pH |

-continued

| Ingredients | per mL |
|---|---|
| Water for Injection | q.s. 1.00 ml |

*Sodium Hydroxide Solution is used to adjust the solution to pH 5.0 or 5.5.
**Sodium Acetate is used to adjust the solution to pH 3.5 or 4.5.
NOTE: Sodium Hydroxide Solution and Sodium Acetate are not combined in the same formulation.

B. Method of Preparation

1. Add and dissolve 8-MOP in Alcohol, USP (200 proof) with mixing.
2. Add and incorporate Propylene Glycol with mixing.
3. Add sufficient Water for Injection to bring the solution to about 95% of final volume and mix.
4. Add Acetic Acid and mix.
5. Add sufficient Sodium Acetate or Sodium Hydroxide Solution with mixing to obtain the desired pH.
6. Add sufficient Water for Injection to bring to final volume and mix.
7. Filter through a suitable bacteria retentive filter into a sterile vial.
8. Aseptically fill into sterile vials, stopper, seal and terminally sterilize.

EXAMPLE 3

Preparation of 8-MOP Lyophilized Powder. 200 µq/Vial

The bulking agent used in this formulation is mannitol, although other substances known to lyophilize well, such as sodium chloride and dextrose, may also be used. The lyophilized powder is reconstituted with 10 ml of a compatible solvent, such as water for injection, to provide a preparation having a concentration of 20 µg/ml.

A. Formulation

| Ingredients | In Process Preparation per 5 mL | Finished Product per Vial |
|---|---|---|
| 8-MOP | 0.20 mg | 0.20 mg |
| Mannitol | 50.00 mg | 50.00 mg |
| Acetic Acid | 0.012 ml | trace |
| Sodium Hydroxide Solution; 10% w/v q.s. | pH 3.5 | trace |
| Water for Injection q.s. | 5.00 ml | * |

*Essentially volatilized during lyophilization.

B. Method of Preparation

1. Heat about 90–95% of the Water for Injection to about 95° C.
2. Add 8-MOP and dissolve with mixing.
3. Cool the solution to room temperature.
4. Add Mannitol and dissolve with mixing.
5. Add Acetic Acid and mix.
6. Add sufficient Sodium Hydroxide Solution with mixing to obtain pH 3.50*.

* This pH was used in this experiment although other acidic pHs could also have been selected.

7. Add sufficient Water for Injection to bring to final volume and mix.
8. Filter through a suitable bacteria retentive filter into a sterile receiver.
9. Aseptically fill into sterile vials, partially stopper with lyophilization stoppers and lyophilize.
10. Seat the stoppers and seal the vials.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A method for the therapy of leukocyte mediated diseases comprising extracorporeal administration to the blood of a subject undergoing ultraviolet-A photophoresis prior to reinfusion of the blood into said subject a composition comprising a sterile aqueous solution of about 0.005 mg/ml to about 1 mg/ml of a psoralen, ethyl alcohol, propylene glycol and water, said composition having a pH from about 2.0 to about 5.5.

2. The method of claim 1 wherein the leukocyte mediated condition is selected from the group consisting of Scleroderma, Systemic Lupus Erythematosis (SLE) Psoriasis, Pemphigus, Psoriatic Arthritis, Atopic Dermatitis, Rheumatoid Arthritis, Multiple Sclerosis.

3. The method of claim 1 wherein the psoralen is 8-MOP.

4. The method of claim 3 wherein the 8-MOP is administered to the patient's blood just after it is withdrawn from the patient and prior to its separation into leukocyte rich and leukocyte poor fractions.

* * * * *